(12) United States Patent
Ulm, III

(10) Patent No.: US 8,900,265 B1
(45) Date of Patent: Dec. 2, 2014

(54) CLOT RETRIEVAL SYSTEM

(71) Applicant: Legacy Ventures LLC, Nashville, TN (US)

(72) Inventor: Arthur John Ulm, III, Nashville, TN (US)

(73) Assignee: Legacy Ventures LLC, Nashville, TN (US)

( * ) Notice: Subject to any disclaimer, the term of this patent is extended or adjusted under 35 U.S.C. 154(b) by 0 days.

(21) Appl. No.: 14/147,491

(22) Filed: Jan. 3, 2014

(51) Int. Cl.
*A61M 29/00* (2006.01)
*A61B 17/221* (2006.01)

(52) U.S. Cl.
CPC .................................. *A61B 17/221* (2013.01)
USPC .......................................... 606/200; 606/159

(58) Field of Classification Search
CPC ............. A61F 2/00; A61F 2/01; A61F 2/013; A61F 2/02
USPC .......................................... 606/192, 194, 200
See application file for complete search history.

(56) References Cited

U.S. PATENT DOCUMENTS

| | | | |
|---|---|---|---|
| 5,895,398 A | 4/1999 | Wensel | |
| 6,336,934 B1 | 1/2002 | Gilson | |
| 6,344,049 B1 | 2/2002 | Levinson | |
| 6,610,077 B1 | 8/2003 | Hancock | |
| 6,635,070 B2 * | 10/2003 | Evans et al. | 606/200 |
| 6,679,893 B1 | 1/2004 | Tran | |
| 7,578,830 B2 | 8/2009 | Kusleika | |
| 7,691,121 B2 | 4/2010 | Rosenbluth | |
| 7,717,935 B2 | 5/2010 | Tsugita | |
| 7,901,427 B2 | 3/2011 | Brady | |
| 8,313,503 B2 | 11/2012 | Cully | |
| 2002/0138094 A1 * | 9/2002 | Borillo et al. | 606/200 |
| 2002/0138097 A1 | 9/2002 | Ostrovsky et al. | |
| 2003/0100918 A1 * | 5/2003 | Duane | 606/200 |
| 2006/0052816 A1 | 3/2006 | Bates | |
| 2008/0091223 A1 | 4/2008 | Pokorney | |
| 2009/0082800 A1 * | 3/2009 | Janardhan | 606/200 |
| 2010/0049240 A1 * | 2/2010 | Papp | 606/200 |
| 2010/0268265 A1 | 10/2010 | Krolik | |
| 2011/0125181 A1 | 5/2011 | Brady | |
| 2011/0213403 A1 | 9/2011 | Aboytes | |
| 2011/0288572 A1 | 11/2011 | Martin | |
| 2012/0059356 A1 | 3/2012 | di Palma | |
| 2012/0165861 A1 | 6/2012 | Palmer | |

FOREIGN PATENT DOCUMENTS

WO    WO2012162437    11/2012

* cited by examiner

*Primary Examiner* — Thomas McEvoy
(74) *Attorney, Agent, or Firm* — Shane V. Cortesi

(57) ABSTRACT

The present invention relates to a system for removing obstructions and other objects within a blood vessel or other interior lumen of an animal. The system may be deployed in the lumen from a catheter and includes a pull wire having a proximal end and a distal end, and a distal body. Optionally, the distal body includes a plurality of memory metal strips that form a closeable claw that is used to capture the obstruction. Optionally, the memory metal strips are connected to a proximal hub that is slideable along at least a segment of the pull wire and the memory metal strips are moved towards each other and towards the pull wire by moving the proximal hub distally towards a stationary distal hub, which in turn, causes the claw to close and capture the obstruction. The present invention also relates to methods of making and using such systems.

30 Claims, 7 Drawing Sheets

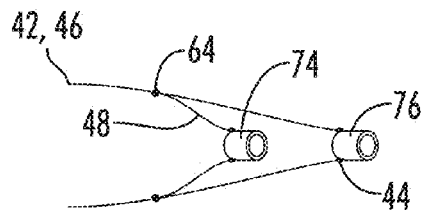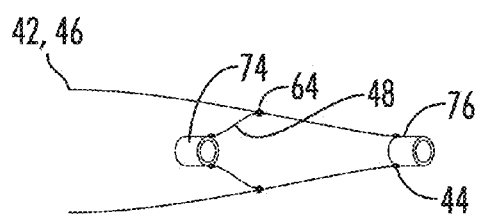
*FIG. 5*      *FIG. 6*
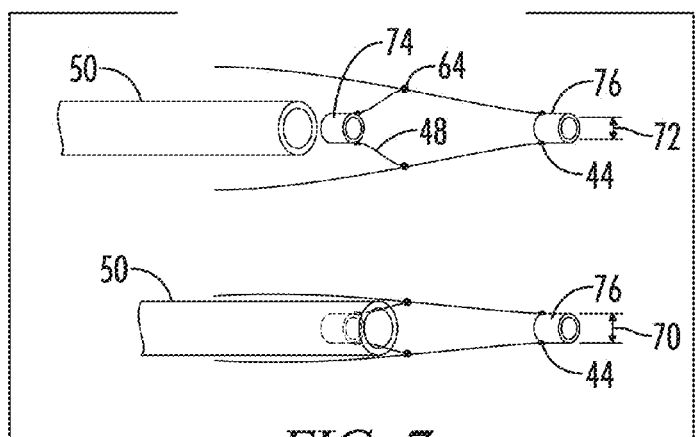
*FIG. 7*
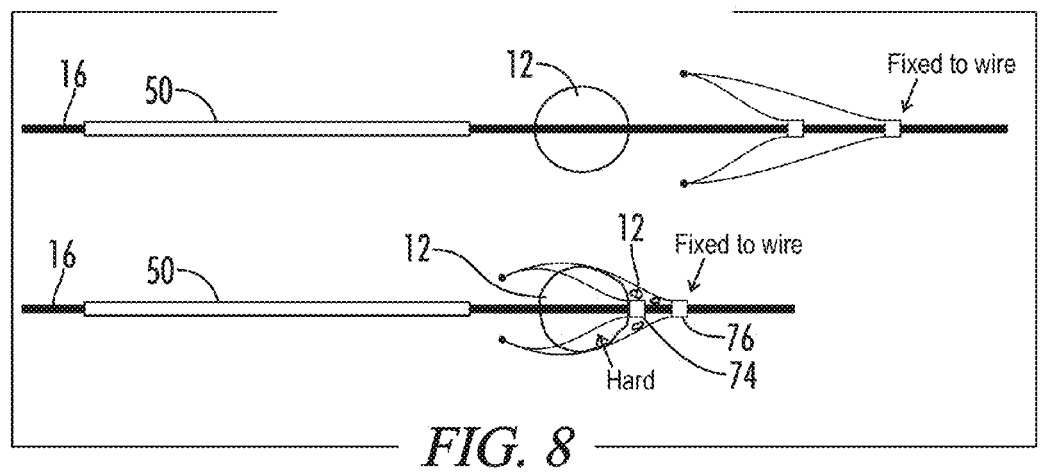
*FIG. 8*

CLOT RETRIEVAL SYSTEM

BACKGROUND

1. Technical Field

The present invention relates to a deployable system for removing a blood clot or other object from a lumen of an animal.

2. Background of the Invention

Acute ischemic strokes develop when a blood clot (thrombus) blocks an artery supplying blood to the brain. Needless to say, when a blood clot creates such a blockage, time in removing the clot is critical.

The removal of intracranial obstructions is limited by several factors, such as the distance of the intracranial obstruction from the femoral access site, the tortuosity (twists and turns in the artery as it enters the base of the skull) of the cervical and proximal intracranial vasculature, the small size of the vessels and the extremely thin walls of intracranial vessels, which lack a significant muscular layer. These limitations require a device to be small and flexible enough to navigate through tortuous vessels within a guide catheter and microcatheter, expand after delivery at the site of occlusion and be retrievable into the microcatheter and yet be strong enough to dislodge strongly adherent thrombus from the vessel wall. In addition, the device should distally entrap or encase the thrombus to prevent embolization to other vessels and to completely remove the occlusion. The device should be retrievable without the need for proximal occlusion of the vessel, which carries risk of further ischemia and risk of vessel injury. The device should be simple to use and be capable of multi-use within the same patient treatment. The device should not be abrasive and should not have sharp corners exposed to the endothelial layer of the vessel wall.

Currently available intravascular thrombus and foreign body removal devices lack several of these features. Currently available devices include the MERCI™ RETRIEVER clot retriever device marketed by Concentric Medical, Inc. (Mountainview, Calif.), the PENUMBRA™ system marketed by Penumbra Inc. (Alameda, Calif.) to retrieve clots, and the newer stent retrieval devices TREVO™ (Stryker, Kalamazoo, Mich.) and SOLITAIRE™ (eV3 Endovascular Inc., Plymouth, Mass., which is a subsidiary of Covidien). All the devices are ineffectual at removing organized hard thrombus that embolize to the brain from the heart and from atherosclerotic proximal vessels. These "hard" thrombi constitute the majority of strokes which are refractory to medical treatment and are therefore referred for removal by mechanical means through an endovascular approach. The MERCI retrieval system is comprised of coiled spring-like metal and associated suture material. The method of use is deployment distal to the thrombus and by withdrawing the device through the thrombus, the thrombus becomes entangled in the coil and mesh and then is retrieved. The MERCI system requires occlusion of the proximal vessel with a balloon catheter and simultaneous aspiration of blood while the thrombus is being removed. Most of the time, the device fails to dislodge the thrombus from the wall of the vessel and often, even when successfully dislodging the thrombus, the thrombus embolizes into another or the same vessel due to the open ended nature of the device.

The next attempt at a thrombus removal system was the PENUMBRA. The PENUMBRA is a suction catheter with a separator that macerates the thrombus which is then removed by suction. The device is ineffective at removing hard, organized thrombus which has embolized from the heart, cholesterol plaque from proximal feeding arteries and other foreign bodies.

The SOLITAIRE and TREVO systems are self-expanding non-detachable stents. The devices are delivered across the thrombus which is then supposed to become entwined in the mesh of the stent and which is then removed in a manner similar to the MERCI system. Again, these devices are ineffectual at treating hard thrombus. In fact, the thrombus is often compressed against the vessel wall by the stent which temporarily opens the vessel by outwardly pressing the clot against the vessel wall. Upon retrieval of the devices, the clot remains or is broken up into several pieces which embolize to vessels further along the vessel.

Thus, there is a need for new, easy-to-use, easy-to-manufacture, safe surgical devices for removing obstructions, such as blood clots, from internal lumens of humans and other animals in a timely manner.

BRIEF SUMMARY

The present disclosure provides a system for removing obstructions and other objects within a blood vessel or other lumen of an animal. The system may be deployed in the lumen from a distal end of a catheter and, in some embodiments, includes a pull wire having a proximal end and a distal end; a distal body attached to the pull wire, the distal body comprising an interior, an exterior, a proximal end, a distal end, a plurality of proximal memory metal strips located at the proximal end, a proximal hub located in the distal body interior, and a distal hub located distal relative to the proximal hub. The distal body has a relaxed state wherein the distal body has a first height and width and a collapsed state wherein the distal body has a second height and width, the second height less than said first height, the second width less than the first width. The system further includes a catheter having an interior, a proximal end leading to the interior and a distal end leading to the interior, the catheter comprised of a biocompatible material and configured to envelope the distal body when the distal body is in the collapsed state. Each of the proximal memory metal strips has a proximal end and a distal end and preferably, in the relaxed state, each of the proximal ends of the proximal memory metal strips is located proximal relative to the proximal hub. Preferably, in the relaxed state, the proximal ends of the proximal memory metal strips are configured to move towards each other and towards the pull wire when an operator moves the proximal hub distally and closer to the stationary distal hub (i.e., when the operator decreases the distance between the hubs). Preferably, in the relaxed state, the proximal ends of the proximal memory metal strips are configured to move away from each other and away from the pull wire by moving the proximal hub proximally away from the stationary distal hub (i.e., when the operator increases the distance between the hubs).

Optionally, the system further includes a plurality of memory metal connector strips, the plurality of memory metal connector strips each having a proximal end attached to a proximal memory metal strip and a distal end attached to the proximal hub. Optionally, the connector strips are integral with the proximal hub (i.e., optionally, the connector strips and the proximal hub are formed from the same piece of memory metal). Optionally, the proximal hub is a tube having an aperture and the pull wire passes through the aperture. Optionally, in the relaxed state, the proximal hub is slideable along the pull wire (i.e., at least a segment of the pull wire). Optionally, in the relaxed state, the proximal memory metal strips are distributed substantially evenly about a perimeter of the distal body. Optionally, the distal hub is a tube having an aperture. Optionally, the distal hub is attached to the pull wire such that the distal hub is not slideable along the pull wire. Optionally, the distal body further comprises a lead wire extending distally from the distal hub. Optionally, the distal body comprises a basket comprised of a plurality of memory metal strips distal relative to the proximal memory metal strips. Optionally, the distal hub, the proximal hub, and the distal basket are comprised of a nitinol having the same material composition. Optionally, the distal body further comprises an x-ray marker configured to be detected by an x-ray radiation of 0.01 mrem when the distal body is located in a cranial blood vessel inside the body of a human and the x-ray is taken from outside the human's body. Optionally, the proximal memory metal strips form a claw, the claw having a closeable proximal end formed by the proximal ends of the proximal memory metal strips. Optionally, between 2 and 4 proximal memory metal strips form the claw. Optionally, the distal body, in the relaxed state, has a tapered shape in which the distal body height and width decrease from the proximal end to the distal end. Optionally, the distal body, in the relaxed state, has a bullet shape. Optionally, the proximal hub and the distal hub are generally cylindrical in shape and each has an outer diameter and an inner diameter that forms the apertures of the proximal and distal hubs, the outer diameters of the proximal and distal hubs are substantially the same size, and the inner diameters of the proximal and distal hubs are substantially the same size. Optionally, the outer diameters of the proximal and distal hubs are from about 0.011 inches to about 0.054 inches, and the inner diameters of the proximal and distal hubs are from about 0.008 inches to about 0.051 inches. Optionally, the pull wire is generally cylindrical and the diameter of the pull wire is between about 0.008 inches and about 0.051 inches. Optionally, the proximal memory metal strips have a length of between about 10 and about 60 millimeters. Optionally, the first height and first width of the distal body are between about 2 millimeters and about 6 millimeters. Optionally, the proximal memory metal strips are configured to a separate a clot from a blood vessel wall.

The present invention also provides a method of removing an object from an interior lumen of an animal, the lumen having an interior wall forming the lumen. In some embodiments, the method includes:

a) providing a system comprising: i) a pull wire having a proximal end and a distal end; ii) a distal body attached to the pull wire, the distal body comprising a proximal end, a distal end, and a claw, the claw comprised of a plurality of memory metal strips, the distal body having a relaxed state wherein the distal body has a first height and width and a collapsed state wherein the distal body has a second height and width, the second height less than said first height, the second width less than said first width; and iii) a catheter having an interior, a proximal end leading to the interior and a distal end leading to the interior, the catheter comprised of a biocompatible material and configured to envelope the distal body when said distal body is in said collapsed state;

b) positioning the system in the lumen;

c) deploying the distal body from the distal end of the catheter;

d) allowing the height and width of said distal body to increase; and e) moving the memory metal strips towards each other and the pull wire so as to capture the obstruction. Optionally, the claw and the memory metal strips are located at the proximal end of said distal body and the distal body is deployed distal to said object. Optionally, the proximal memory metal strips have a proximal end forming the proximal end of the claw and a distal end, and the method includes moving the proximal ends of the memory metal strips towards each other and the pull wire so as to capture the obstruction. Optionally, the distal body further comprises a proximal hub located in the distal body interior, and a distal hub located distal relative to the proximal hub, each of the memory metal strips has a proximal end and a distal end, each of the proximal ends of the memory metal strips is located proximal relative to the proximal hub, and the proximal ends of the memory metal strips are configured to move towards each other and towards the pull wire by moving the proximal hub distally and closer to the distal hub, and the proximal ends of the memory metal strips are configured to move away from each other and away from the pull wire by moving the proximal hub proximally and away from the distal hub, and the method further comprises moving the proximal hub distally and closer to the distal hub so as to capture the obstruction in the claw. Optionally, the interior lumen is an intracranial artery and the obstruction is a blood clot. Optionally, the method further comprises using the clot to move the proximal hub toward the distal hub and exert tension on the proximal memory metal strips. Optionally, the method further comprises using a tube to move the proximal hub toward the distal hub and exert tension on the proximal memory metal strips.

The present invention also provides a method of manufacturing a system for removing objects within an interior lumen of an animal. In some embodiments, the method includes:

a) providing a single tube comprised of a memory metal, the single tube having an exterior, a hollow interior, a wall separating the exterior from the hollow interior, a proximal portion comprising an aperture leading to the hollow interior, a distal portion comprising an aperture leading to the hollow interior, and a middle portion between the proximal portion and the distal portion;

b) cutting the wall of the middle portion with a laser;

c) removing the pieces of the middle portion cut by the laser to form a proximal tube, a middle portion comprising a plurality of memory metal strips attached to the proximal tube and a distal tube;

d) altering the shape of the middle portion;

e) allowing the middle portion to expand relative to the distal tube and the proximal tube;

f) cutting the memory metal strips to form a first segment comprising the proximal tube and a proximal segment of the memory metal strips, and a second segment comprising the distal tube and a distal segment of the memory metal strips; and g) joining the proximal segments to the distal segments such that the distal segments form the proximal end of a distal body, such that the proximal tube is located inside an interior of said distal body, and such that the proximal tube is located distal relative to the proximal end.

Optionally, the method further includes placing a pull wire through the proximal tube such that the proximal tube is slideable along at least a segment of the pull wire. Optionally, the method further includes attaching the pull wire to the distal tube. Optionally, the step of joining the proximal segments to the distal segments comprises welding the proximal segments to the distal segments. Optionally, after the step of joining the proximal segments to the distal segments, the proximal end forms a claw comprised of between 2 and 4 memory metal strips, the claw memory metal strips configured to move towards each by moving said proximal tube distally and closer to the distal tube, and the claw memory metal strips configured to move away from each other by moving the proximal tube proximally and away from said distal tube. Optionally, the method further includes not altering the shape of the proximal and distal portions while altering the shape of the middle portion. Optionally, the method further includes cooling the proximal portion, the middle portion, and the distal portion after step D) and, after cooling, the proximal and distal portions have substantially the same size as the proximal and distal portions had prior to step A). Optionally, the method of allowing said middle portion to expand comprises heating the middle portion. Optionally, the method of altering the shape of the middle portion comprises using a mandrel. Optionally, the mandrel is tapered. Optionally, the proximal portion and the distal portion are not cut by the laser. Optionally, prior to cutting the memory metal tube, the memory metal tube has an outer diameter that is from about 0.011 inches to about 0.054 inches and an inner diameter that is from about 0.008 inches to about 0.051 inches.

BRIEF DESCRIPTION OF THE DRAWINGS

in FIG. 2a, the tube is shown as though it were flat for purposes of illustrating the cut pattern only.

in FIG. 2c, the tube is rotated as compared to FIG. 2b.

in FIGS. 3A-3H, the basket portion of the distal body is not shown for simplicity of illustration.

in FIGS. 4A-4D, the basket portion of the distal body is not shown for simplicity of illustration.

FIGS. 5 and 6 illustrate different locations that connector strips may be welded to the proximal memory metal strips.

FIG. 7 illustrates a side, elevation view of a catheter and the distal body of FIG. 6.

FIG. 8 illustrates a side, elevation view of a deployable system of one embodiment of the present invention being used to capture a blood clot; in FIG. 8, the basket portion of the distal body is not shown for simplicity of illustration.

in FIG. 9, the basket portion of the distal body is not shown for simplicity of illustration.

in FIG. 10, the basket portion of the distal body is not shown for simplicity of illustration.

DETAILED DESCRIPTION

Figure 1A:
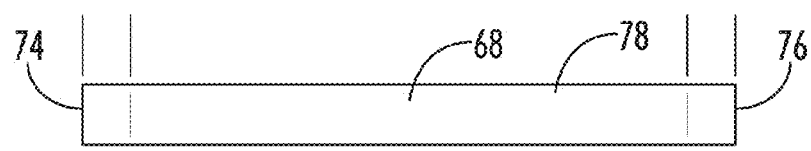
FIG. 1A illustrates a side, elevation view of a memory metal tube prior to being cut by a laser.
Figure 1B:
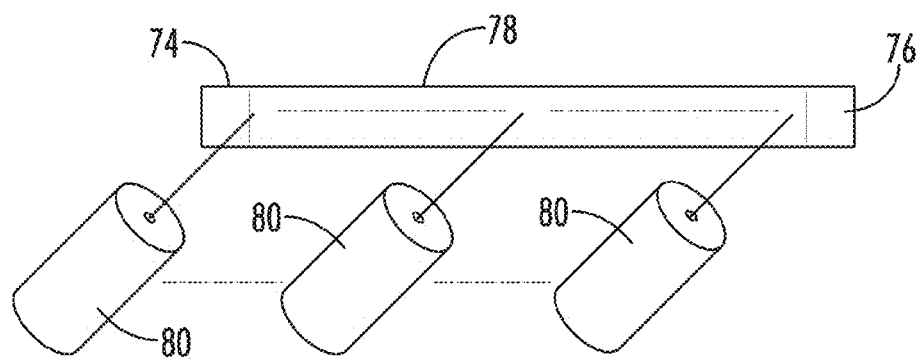
FIG. 1B illustrates a side, elevation view of the memory metal tube of FIG. 1A being cut by a laser.

With reference to FIGS. 1-10, the present disclosure provides a deployable system, generally designated by the numeral 10, for removing an obstruction such as a blood clot 12 or other object from a blood vessel 14 or other interior lumen of an animal. In addition to a blood clot 12, the obstruction may be, for example, extruded coils during aneurysm treatment, intravascular embolic material such as onyx or other obstructions requiring mechanical intravascular removal from small distal vessels. In the drawings, not all reference numbers are included in each drawing for the sake of clarity.

Referring further to FIGS. 1-10, the deployable system 10 includes a pull wire 16 that has a proximal end (not shown) and a distal end 20. Optionally, the diameter of the pull wire is between about 0.008 inches and about 0.051 inches.

The system 10 further includes a distal body 22, which is attached to the pull wire 16. The distal body 22 has a proximal end 24, a distal end 26, an interior 28, and an exterior 30. The distal body 22 has a collapsed state, wherein the distal body 22 has a first height and width and is configured to fit into a catheter 50 (see FIG. 10A), and a relaxed state wherein the distal body 22 has a different height 32 and width and is configured to expand to about the height and width of a human blood vessel 14 when the distal body 22 is deployed from the catheter 50 (see FIGS. 10B-G). The distal body 22 further includes a proximal hub 74 and a distal hub 76 that is located distal relative to the proximal hub 74. In some embodiments, the distal body 22 includes a plurality of strips 40 comprised of a memory metal (e.g., a memory metal alloy such as nitinol) that form the proximal end 24 of the distal body 22. Optionally, the proximal memory metal strips 40 each have a distal end 44 and a proximal end 42 that forms an openable and closeable claw 46. Optionally, the proximal memory metal strips 40 are attached to the proximal hub 74 through connector memory metal strips 48. In such embodiments, the proximal hub 74 may be slideable along at least a segment of the pull wire 16, in contrast to the distal hub 76, which is optionally fixed to the pull wire 16 and not slideable along the pull wire 16. Moving the proximal hub 74 distally and closer to the distal hub 76 (i.e., shortening the distance 88 between the proximal hub 74 and distal hub 76 by moving the proximal hub 74 distally while keeping the distal hub 76 stationary) exerts tension on the connector memory metal strips 48 and, in turn, the proximal memory metal strips 40. This tension, in turn, causes the proximal ends 42 of the proximal memory metal strips 40 to move radially toward each other and the pull wire 16. As the proximal ends 42 of the proximal memory metal strips 40 move radially toward each other and the pull wire 16, the claw 46 (formed by the proximal memory metal strips 40) is brought from the open position to at least a partially closed position, which in turn, separates the obstruction 12 from the wall of the human lumen 14 and captures the obstruction 12. See FIG. 3H, FIG. 8, FIG. 9F, and FIGS. 10F and 10G. Conversely, preferably, movement of the proximal hub 74 proximally and away from the distal hub 76 (i.e., increasing the distance 88 between the hubs 74 and 76) releases the tension in the proximal memory metal strips 40, which in turn, causes the proximal ends 42 of the proximal memory metal strips 40 to move away from each other and the pull wire 16, opening the claw 46. The claw 46 and proximal hub 74 form several functions. First, as described, closing of the claw 46 captures the obstruction 12. Second, closing the claw 46 retracts the claw 46 from the wall of the lumen 14 so that the claw 46 does not scrape against (and damage) the lumen wall while capturing the obstruction 12. Third, closing the claw 46 reduces the height and width of the distal body 22, which allows the distal body 22 to be re-sheathed in the catheter 50, which may be desired, for example, if the operator seeks to re-deploy the distal body 22 in another location in the body (which may be the case if the operator originally deploys the distal body 22 in the wrong location in the lumen 14). For purposes of the present invention, "closing the claw" embraces both partially closing the claw 46 (where the proximal ends 42 of the proximal memory metal strips 40 do not contact the pull wire 16) and fully closing the claw 46 (where the proximal ends 42 contact the pull wire 16).

The claw 46 may be comprised of any number of proximal memory metal strips 40. Preferably, however, between 2 and 4 proximal memory metal strips 40 comprise the claw 46 (it being understood that the connector strips 48, if present, merely serve to tether the claw 46 to the proximal hub 74). Preferably, the proximal memory metal strips 40 have a length of between about 10 and about 60 millimeters. The proximal memory metal strips 40 can be thought of as arms of the claw 46.

In some embodiments, the connector strips 48 are integral with the proximal hub 74 (i.e., formed from the same piece of memory metal). In other embodiments, the proximal hub 74 may be welded to the connector strips 48. Optionally, in the relaxed state, the proximal memory metal strips 42 are distributed substantially evenly about a perimeter of the distal body 22.

Optionally, the distal body 22 includes a lead wire 52 extending distally from the distal body 22. Optionally, the lead wire 52 extends distally from the distal hub 76. If present, the lead wire 52 may be used to facilitate movement of the system 10 in the lumen 14.

Figure 2:
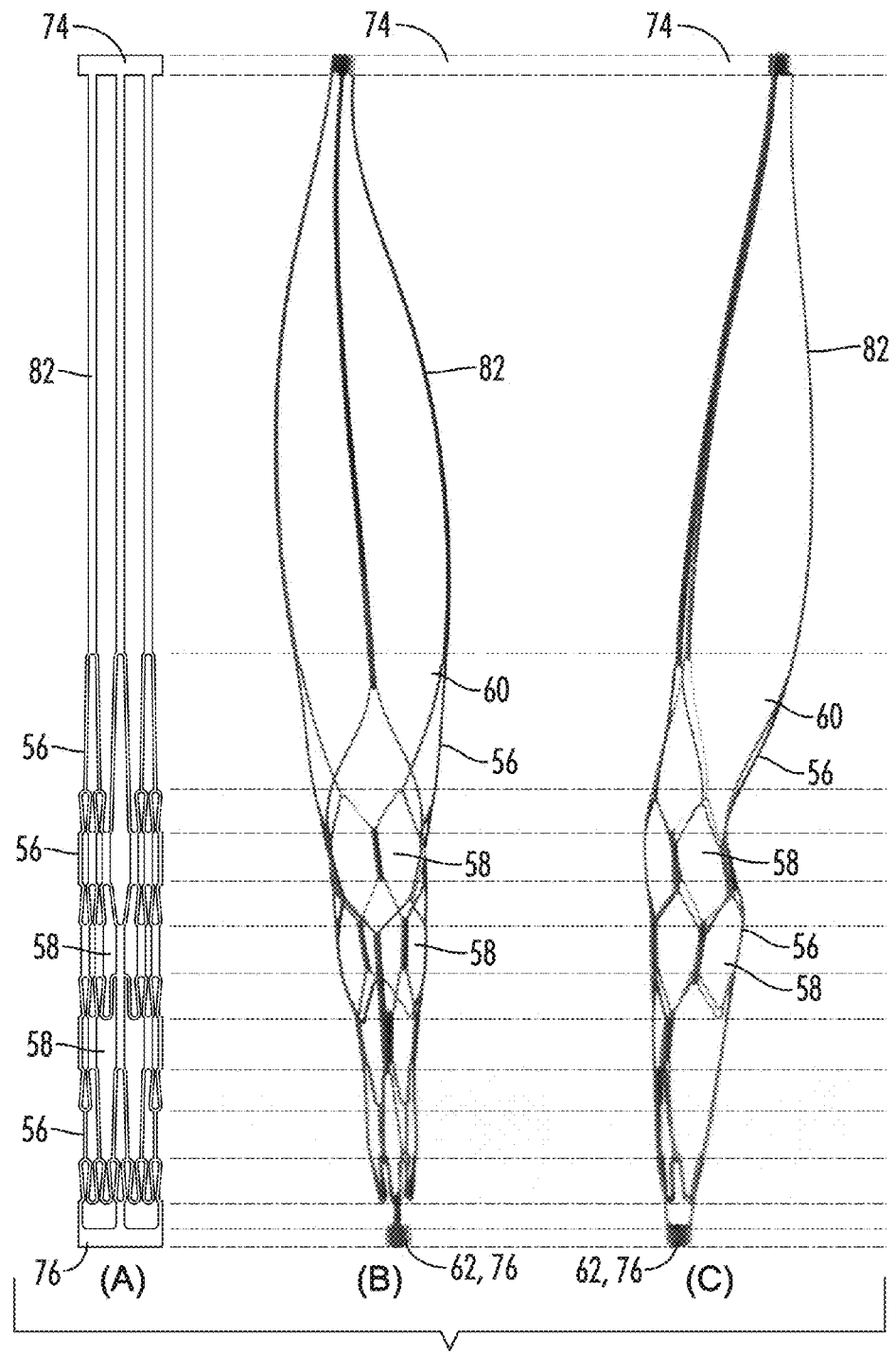
FIG. 2a illustrates a side, elevation view of the memory metal tube of FIG. 1B after being cut by a laser.
FIG. 2b illustrates a side, perspective view of the memory metal tube of FIG. 1B after being cut by a laser.
FIG. 2c illustrates another side, perspective view of the memory metal tube of FIG. 1B after being cut by a laser.

Optionally, the distal body 22 includes a basket 54 distal to the proximal memory metal strips 40, the basket 54 comprised of a plurality of memory metal strips 56 distal relative to the proximal memory metal strips 40. The distal memory metal strips 56 may, for example, form a basket 54 with a plurality of mesh openings 58. Optionally, the size of the mesh openings 58 in the basket 54 when the distal body 22 is in its relaxed state is less (preferably significantly less) than the diameter of an average-sized ischemic blood clot 12 so that the blood clot 12 does not escape from the distal basket 54 after being captured by the distal body 22. Optionally, the basket 54 has an open proximal end 60 and a substantially closed distal end 62, which is formed by distal tube 76. Optionally, the distal and proximal hubs 74 and 76 and the distal basket 54 are comprised of a nitinol having the same material composition. Optionally, the size of the mesh openings 58 decreases from the proximal end 60 of the basket 54 to the distal end 62. The distal basket 54 is best seen in FIG. 2 and can be comprised of a different number of cell patterns. The distal basket 54 is not shown in FIGS. 3-10 for ease of illustrating the other components in the system 10.

Optionally, the proximal hub 74 and the distal hub 76 are cylindrical tubes comprising substantially circular apertures that span the length of the hubs 74 and 76 and the hubs 74 and 76 have approximately the same inner diameter 72 and the same outer diameter 70. Preferably, the inner diameter 72 is at least slightly larger than the diameter of the pull wire 16 so that the pull wire 16 can slide through the proximal hub 74. In some embodiments, the outer diameters 70 of the proximal and distal hubs 74 and 76 may be from about 0.011 inches to about 0.054 inches and the inner diameters 72 of the proximal and distal hubs 74 and 76 may be from about 0.008 inches to about 0.051 inches.

Optionally, the distal body 22 further comprises an x-ray marker 64 configured to be detected by an x-ray radiation of 0.01 mrem when the distal body 22 is located in a cranial blood vessel inside the body of a human and the x-ray is taken from outside the human's body. If the connector strips 48 are welded to the proximal memory metal strips 40, the x-ray markers 64 may be, for example, located at the welding site. In some cases, the increased thickness at the welding site may in of itself comprise the x-ray marker 64.

A catheter 50 with an open proximal end (not shown) and an open distal end 66 initially envelopes the system 10. As used herein, the term "catheter" generally refers to any suitable tube through which the system 10 can be deployed. Preferably, the catheter 50 is sterile and comprised of a biocompatible material (i.e., a material that does not irritate the human body during the course of a 45 minute operation that involves using the system 10 to remove a clot 12 from an intracranial blood vessel 14). The catheter 50 can be any suitable shape, including but not limited to generally cylindrical. Preferably, the catheter 50 is a microcatheter. For purposes of the present invention, when it is said that the catheter 50 envelopes the system 10, it will be understood that the catheter 50 envelopes at least one component of the system 10 (preferably, the distal body 22, the lead wire 52, and the pull wire 16). In some embodiments, the catheter 50 is about 2.5 French in diameter. Optionally, the catheter 50 is delivered to the region of the lumen 14 that has the obstruction 12 as follows: a guide wire is delivered to the obstruction region past the obstruction 12; the catheter 50 is delivered over the guide wire; the guide wire is removed; and the system 10 is delivered with its pull wire 16 and lead wire 52 through the catheter 50. Optionally, the pull wire 16 is used to push the system 10 through the catheter 50 as well as to retrieve the distal body 22 after capturing the obstruction 14 as described below. The system 10 may utilize a plurality of catheters 50, such as, for example, a wider catheter that travels to the brain and a very flexible, smaller diameter microcatheter that is delivered from the first catheter and travels through the small arteries of the brain.

Optionally, in the relaxed, opened-claw state, the distal body 22 or optionally just the distal basket 54 has a tapered shape (e.g., substantially conical or bullet in shape) so that the distal body 22 or just the distal basket 54 tapers from the distal body 22 or the distal basket's 54 proximal end to the distal end.

The proximal end of the system 10 is shown at the left end of FIGS. 1 and 3-10 and the distal end of the system 10 is shown at the right end of FIGS. 1 and 3-10 because a principal use of the system 10 is to remove a blood clot 12 from a human intracranial artery 14, in which case the system 10 generally will enter the artery 14 at its proximal end by the surgeon entering the patient's body near the groin and pushing the catheter 50 towards the brain. The diameter of human arteries 14 generally decrease from their proximal end to their distal end. However, when used in other types of lumens, the distal body 22 may be located proximally relative to the catheter 50 as the term proximally and distally are used in that lumen.

The surgeon may deploy the distal body 22 by, for example, moving the catheter 50 proximally so as to unsheathe the distal body 22 or by pushing the distal body 22 out of the catheter 50.

Use of the system 10 will now be described to remove a blood clot 12 from an intracranial artery 14 of a human ischemic stroke patient, however, it will be appreciated that the system 10 may be used to remove other objects from other interior lumens.

A catheter 50, which contains the collapsed distal body 22 is positioned in the lumen 14 distal to the clot 12. See FIG. 10A.

The distal body 22 is deployed from the catheter 50 and the height and width of the distal body 22 expand to about the height and width of the blood vessel 14. See FIG. 10B.

The catheter 50 is pulled proximally and a claw-actuator tube 90 is deployed into the blood vessel 14. See FIG. 10C.

The distal body 22 is moved proximally so that the clot 12 is located in the interior 28 of the distal body 22. See FIGS. 10D and 10E.

The claw-actuator tube 90 is moved distally, which pushes the proximal hub 74 distally so that the distance 88 between the proximal hub 74 and the distal hub 76 (which is fixed to the pull wire 16 and kept stationary) decreases. Distal movement of the proximal hub 74 exerts tension on the connector and proximal memory metal strips 40 and 48, which in turn, closes the claw 46. See FIG. 10F. (The claw actuator tube 90 should float on the pull wire 16—i.e., have an aperture extending the tube's length that has a diameter larger than the diameter of the pull wire 16—and the aperture of the claw actuator tube 90 should be smaller than the diameter of the proximal hub 74 so that the claw actuator tube 90 pushes the proximal hub 74).

The system 10 is withdrawn proximally and removed from the body. See FIG. 10G.

To test the efficacy of the system 10, a distal body 22 with a distal basket 54, proximal and distal hubs 74 and 76, and a claw 46 comprised of three proximal memory metal strips 42 was tested in a flow model that included a tube and a moist cotton ball located in the tube. The cotton ball was used to simulate a blood clot. The system 10 was deployed distal to the cotton ball. The claw 46 was closed by moving the proximal hub 74 distally to capture the cotton ball. The system 10 and cotton ball were withdrawn proximally in the tube.

Figure 3:
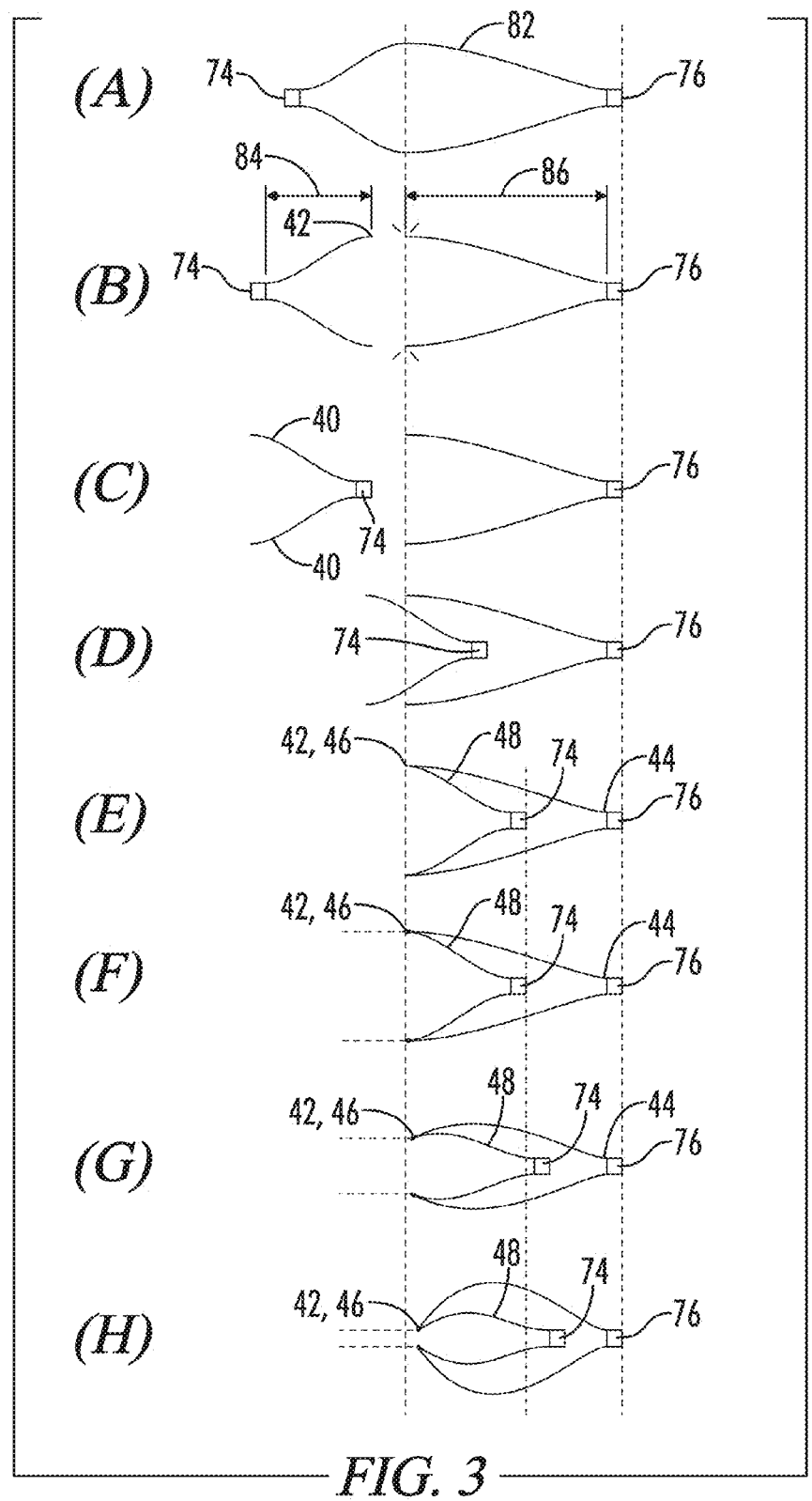
FIGS. 3A-3H illustrate a method of manufacturing a distal body of one embodiment of the present invention using the laser cut memory metal tube of FIGS. 1 and 2.
Figure 4:
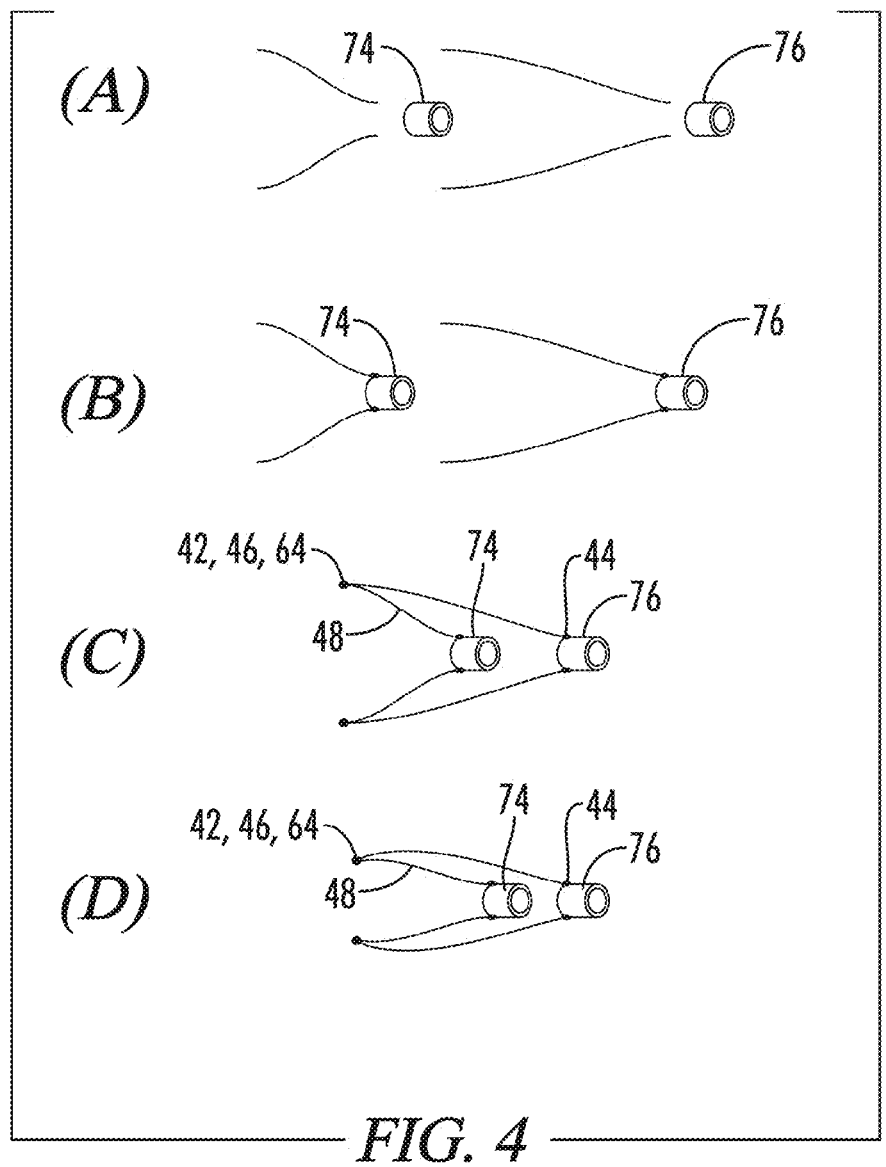
FIGS. 4A-4D illustrate the welding steps of the method of manufacturing shown in FIG. 3.
Figure 9:
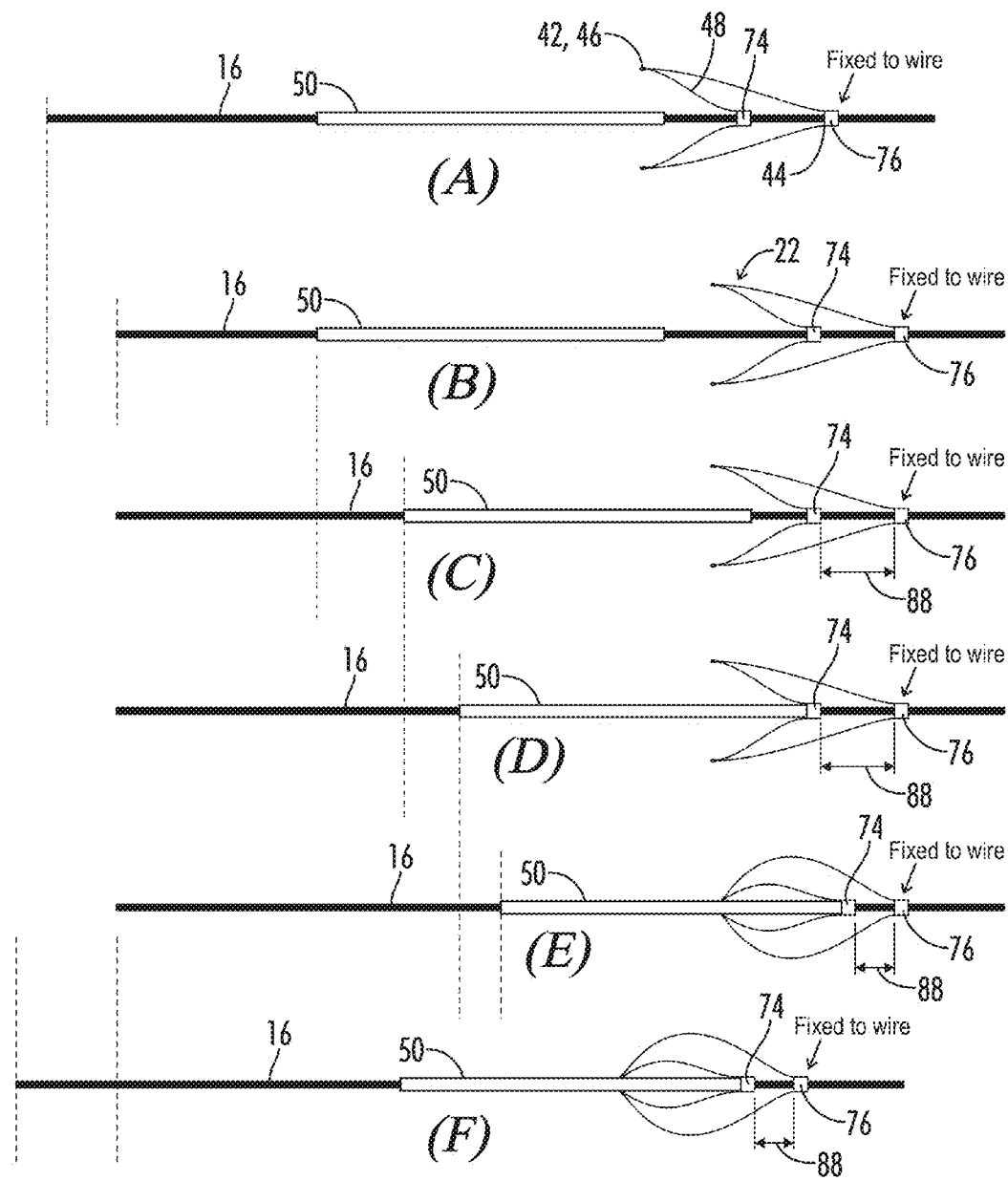
FIG. 9 illustrates a side, elevation view of a claw of one embodiment of the present invention being closed by a claw actuator tube.
Figure 10:
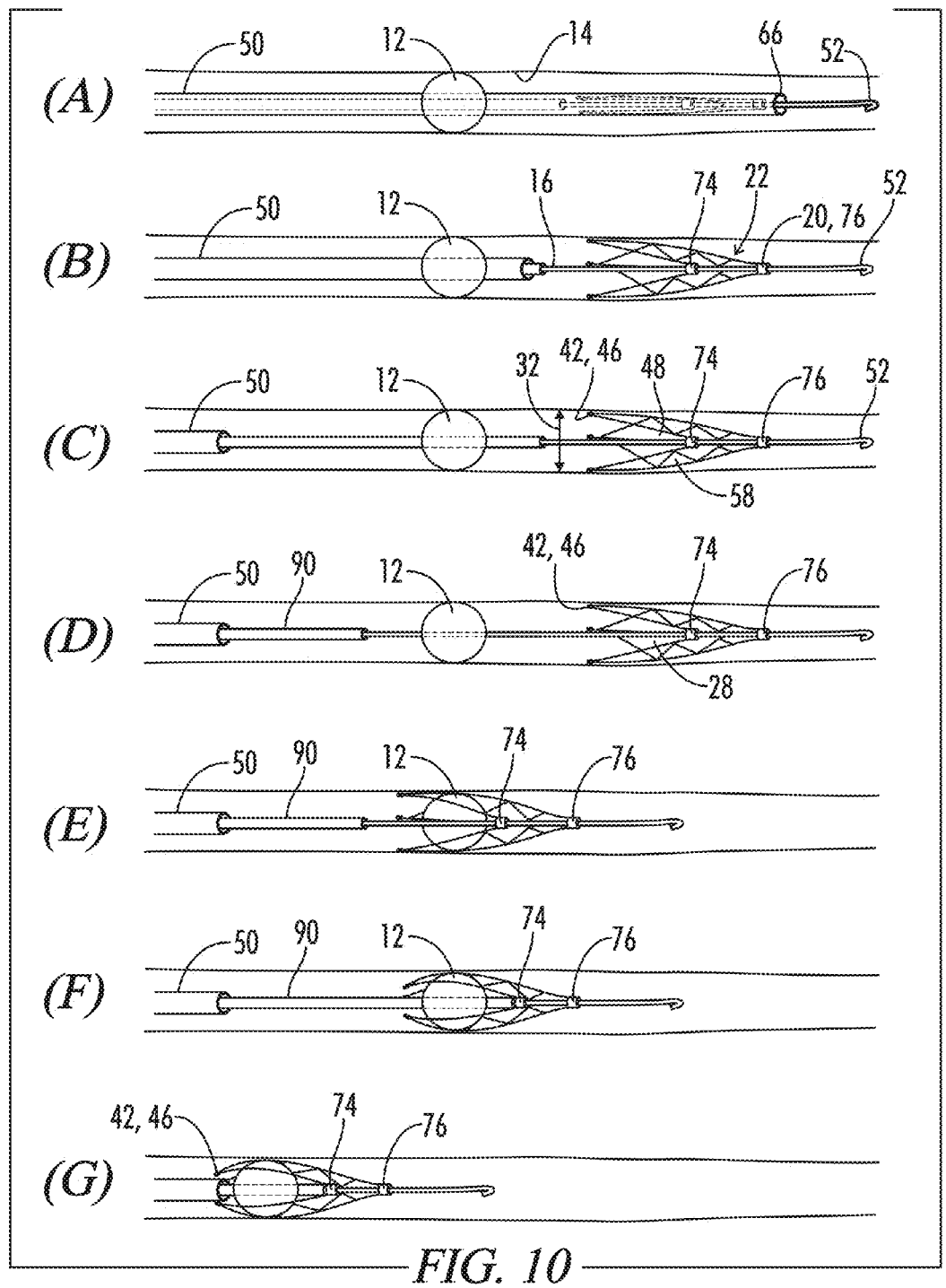
FIG. 10 illustrates a side, elevation view of a deployable system of one embodiment of the present invention being used to capture a blood clot.

In some embodiments, the distal body 22 is prepared by a process that includes one or more of the following steps, as illustrated in FIGS. 1-4
a) providing a single tube 68 comprised of a memory metal such as nitinol, the single tube 68 having an exterior, a substantially hollow interior, a wall separating the exterior from the substantially hollow interior, an open proximal end 74, an open distal end 76, a middle portion 78 between the open proximal end 74 and the open distal end 76 (see FIG. 1A);
b) cutting the wall of the middle portion 78 with a laser 80 (see FIG. 1B);
c) removing the pieces of the middle portion 78 cut by the laser 80 to form a proximal tube 74, a distal tube 76 and a middle portion 78 comprising a plurality of memory metal strips 82 attached to the proximal tube 74;
d) altering the shape of the middle portion 78 using a mandrel and allowing the middle portion 78 to expand relative to the distal tube 76 and proximal tube 74 to form the distal basket 54;
e) quenching the middle portion 78 at room temperature;
f) removing the mandrel from the middle portion 78 (see FIGS. 2 and 3A);
g) mechanically or chemically electropolishing the middle portion 78 to remove oxides;
h) cutting the memory metal strips 82 to form a first segment 84 comprising the proximal tube 74 and a proximal segment of the memory metal strips 82 and a second segment 86 comprising the distal tube 76 and a distal segment of the memory metal strips 82 (see FIG. 3B); and
i) joining the proximal segments to the distal segments such that the distal segments form the proximal end 24 of the distal body 22, such that the proximal tube 74 is located inside the interior 28 of the distal body 22, and such the proximal tube 74 is located distal relative to the distal body proximal end 24 (see FIGS. 3C-3E).

In some embodiments, the method further includes placing the pull wire 16 through the proximal tube 74 so that the proximal tube 74 is slideable along at least a segment of the pull wire 16.

In some embodiments, the method further includes attaching the pull wire 16 to the distal tube 76 so that the distal tube 76 is not slideable along the pull wire 16 but instead the distal tube 76 moves with the pull wire 16.

In some embodiments, after step i, the proximal end 24 of the distal body 22 forms a claw 46 comprised of between 2 to 4 proximal memory metal strips 40, the claw proximal memory metal strips 40 configured to move towards each other and the pull wire 16 by moving the proximal tube 74 distally and toward the distal tube 76 (i.e., decreasing the distance 88 between the tubes 74 and 76) and the claw memory metal strips 40 configured to move away from each other and away from the pull wire (i.e., increasing the distance 88 between the tubes 74 and 76) by moving the proximal tube 76 proximally and away from the distal tube 76 (as described previously).

In some embodiments, the middle portion 78 is expanded by heating the mandrel and the middle portion 78 by, for example, placing the mandrel and the middle portion 78 in a fluidized sand bath at about 500° C. for about 3 to about 7 minutes. As the middle portion 78 is heated, the heating causes the crystalline structure of the memory metal tube 68 to realign. Preferably, the mandrel is tapered (e.g., substantially conical or bullet in shape) so that the distal basket 54 formed from the middle portion 78 tapers from the proximal end 60 to the distal end 62. Preferably, the proximal and distal ends of the tube 74 and 76 are not shape set by the mandrel and are not cut by the laser 80 so that the proximal and distal ends 74 and 76 do not change in shape and only slightly expand in size under heating and return to the size of the native tube 68 after the heat is removed. Preferably, the laser cuts are programmed via a computer. To ensure that the laser cuts only one surface of the tube wall at the time (and not the surface directly opposite the desired cutting surface), the laser 80 is preferably focused between the inner and outer diameter of the desired cutting surface and a coolant is passed through the memory metal tube 68 so that the laser 80 cools before reaching the surface directly opposite the desired cutting surface.

The portions of the wall not cut by the laser 80 create the distal basket 53, proximal and distal tubes 74 and 76, and memory metal strips 40, 48 and 56, as described.

Preferably, the memory metal selected for the native tube 68 has a heat of transformation below average human body temperature (37° C.) so that the distal body 22 has sufficient spring and flexibility after deployment from the catheter 50 in the human blood vessel 14.

In some embodiments, the native tube 68 (and hence the distal and proximal tubes 74 and 76) have an outer diameter of less than about 4 French, e.g., a diameter of about 1 to about 4 French. In some embodiments, the diameter of the pull wire 16 is between about 0.008 inches and about 0.051, as noted above, and in such embodiments, the diameter of the pull wire 16 may be approximately equal to the inner diameter 72 of the native nitinol tube 68.

Without being bound by any particular theory, it is believed that manufacturing the distal body 22 from a single memory metal tube 68 provides ease of manufacturing and safety from mechanical failure and provides tensile strength necessary for the system 10 to remove hard thrombus 12 and other obstructions.

Having now described the invention in accordance with the requirements of the patent statutes, those skilled in the art will understand how to make changes and modifications to the disclosed embodiments to meet their specific requirements or conditions. Changes and modifications may be made without departing from the scope and spirit of the invention, as defined and limited solely by the following claims. In particu- lar, although the system has been exemplified for use in retrieving blood clots, the system may be used to retrieve other objects from animal lumens. In addition, the steps of any method described herein may be performed in any suitable order and steps may be performed simultaneously if needed.

Terms of degree such as "substantially", "about" and "approximately" as used herein mean a reasonable amount of deviation of the modified term such that the end result is not significantly changed. For example, these terms can be construed as including a deviation of at least ±5% of the modified term if this deviation would not negate the meaning of the word it modifies.

What is claimed is:

1. A system for removing objects adhered to a wall of an interior lumen of an animal, the system comprising:
   a pull wire having a proximal end and a distal end;
   a distal body attached to said pull wire, said distal body comprising an interior, an exterior, a proximal end, a distal end, a plurality of proximal memory metal strips located at said proximal end, a proximal hub located in said distal body interior, and a distal hub located distal relative to said proximal hub, said distal body having a relaxed state wherein said distal body has a first height and width, and a collapsed state wherein said distal body has a second height and width, said second height less than said first height, said second width less than said first width;
   a catheter having an interior, a proximal end leading to said interior and a distal end leading to said interior, said catheter comprised of a biocompatible material and configured to envelope said distal body when said distal body is in said collapsed state;
   wherein each of said proximal memory metal strips has a proximal end and a distal end,
   wherein, in said relaxed state, each of said proximal ends of said memory metal strips is located proximal relative to said proximal hub,
   wherein, in said relaxed state, said proximal ends of said proximal memory metal strips are configured to move towards each other and towards said pull wire, while remaining a fixed distance from said distal hub, by moving said proximal hub distally towards said distal hub,
   wherein, in said relaxed state, said proximal ends of said proximal memory metal strips are configured to move away from each other and away from said pull wire, by moving said proximal hub proximally and away from said distal hub, and
   wherein said proximal memory metal strips are configured to remove an object adhered to a wall of an interior lumen of an animal.

2. The system of claim 1 further comprising a plurality of memory metal connector strips, the plurality of memory metal connector strips each having a proximal end attached to a proximal memory metal strip and a distal end attached to said proximal hub and further wherein, in said relaxed state, said proximal ends of said memory metal connector strips are configured to move towards said pull wire upon moving said proximal hub distally towards said distal hub and said movement of said memory metal connector strips is configured to cause said proximal ends of said proximal memory metal strips to move towards each other and towards said pull wire.

3. The system of claim 2, wherein said connector strips are integral with said proximal hub.

4. The system of claim 1, wherein said proximal hub is a tube having an aperture and said pull wire passes through said aperture.

5. The system of claim 4, wherein, in said relaxed state, said proximal hub is slideable along at least a segment of said pull wire distal to said proximal hub and further wherein said distal hub is attached to said pull wire such that said distal hub is not slideable along said pull wire.

6. The system of claim 1, wherein, in said relaxed state, said proximal memory metal strips are distributed substantially evenly about a perimeter of the distal body.

7. The system of claim 1, wherein said distal hub is a tube having an aperture, wherein said pull wire extends from said proximal hub to said distal hub and further wherein said distal hub is attached to said pull wire such that said distal hub is not slideable along said pull wire.

8. The system of claim 1, wherein said pull wire extends from said proximal hub to said distal hub and further wherein said distal hub is attached to said pull wire such that said distal hub is not slideable along said pull wire.

9. The system of claim 1, wherein said distal body further comprises a lead wire extending distally from said distal hub.

10. The system of claim 1, wherein said distal body comprises a basket comprised of a plurality of memory metal strips distal relative to said proximal memory metal strips.

11. The system of claim 10, wherein said distal hub, said proximal hub, and said distal basket are comprised of a nitinol having the same material composition.

12. The system of claim 1, wherein said distal body further comprises an x-ray marker configured to be detected by an x-ray radiation of 0.01 mrem when the distal body is located in a cranial blood vessel inside the body of a human and the x-ray is taken from outside the human's body.

13. The system of claim 1, wherein said proximal memory metal strips form a claw, said claw having a closeable proximal end formed by said proximal ends of said proximal memory metal strips.

14. The system of claim 13, wherein between 2 and 4 proximal memory metal strips form said claw.

15. The system of claim 1, wherein said distal body, in said relaxed state, has a tapered shape in which the distal body height and width decrease from the proximal end to the distal end.

16. The system of claim 15, wherein said distal body, in said relaxed state, has a bullet shape.

17. The system of claim 1, wherein said proximal and said distal hubs are generally cylindrical in shape and each has an outer diameter and an inner diameter, the inner diameter forming apertures of the proximal and distal hubs and further wherein the outer diameters of the proximal and distal hubs are substantially the same size and further wherein the inner diameters of the proximal and distal hubs are substantially the same size.

18. The system of claim 17, further wherein the outer diameters of the proximal and distal hubs are from about 0.011 inches to about 0.054 inches, and further wherein the inner diameters of the proximal and distal hubs are from about 0.008 inches to about 0.051 inches.

19. The system of claim 1, wherein the pull wire is generally cylindrical and further wherein the diameter of the pull wire is between about 0.008 inches and about 0.051 inches.

20. The system of claim 1, wherein said proximal memory metal strips have a length of between about 10 and about 60 millimeters.

21. The system of claim 1, wherein the first height and first width of the distal body are between about 2 millimeters and about 6 millimeters.

22. The basket system of claim 1, wherein the proximal memory metal strips are configured to separate a clot from a blood vessel wall.

23. The system of claim 1, wherein said proximal ends of said proximal memory metal strips are not connected to each other.

24. The system of claim 1, wherein, in said relaxed state, said interior of said distal body is hollow.

25. A method of removing an object adhered to a wall of an interior lumen of an animal, the method comprising the steps of:
   a) providing the system of claim 1;
   b) positioning the system in said lumen;
   c) deploying said distal body from said distal end of said catheter;
   d) allowing said height and width of said distal body to increase; and
   e) moving said proximal memory metal strips towards each other and said pull wire so as to capture said object.

26. The method of claim 25, wherein said distal body is deployed distal to said object.

27. The method of claim 25, wherein said method further comprises moving said proximal hub distally and closer to said distal hub so as to capture said object.

28. The method of claim 27, wherein said interior lumen is an intracranial artery and said object is a blood clot.

29. The method of claim 28, wherein said method further comprises using said blood clot to move said proximal hub toward said distal hub and exert tension on said proximal memory metal strips.

30. The method of claim 28, wherein said method further comprises using a tube to move said proximal hub toward said distal hub and exert tension on said proximal memory metal strips.

* * * * *